United States Patent [19]

Papantoniou et al.

[11] 4,032,628
[45] June 28, 1977

[54] COSMETIC EMULSION COMPOSITIONS INCLUDING BLOCK POLYMER EMULSIFIERS

[75] Inventors: Christos Papantoniou, Epinay-sur-Seine; Rose-Marie Handjani, Paris, both of France

[73] Assignee: Societe Anonyme dite: L'Oreal, Paris, France

[22] Filed: Nov. 5, 1975

[21] Appl. No.: 628,906

Related U.S. Application Data

[63] Continuation of Ser. No. 294,923, Oct. 4, 1972, abandoned, which is a continuation-in-part of Ser. No. 131,810, April 6, 1971, abandoned.

[30] Foreign Application Priority Data

Oct. 6, 1971 France .......................... 71.36878
Apr. 7, 1970 France .......................... 70.60676

[52] U.S. Cl. .................... 424/63; 252/309; 252/312; 252/356; 252/357; 424/69; 424/78; 424/81; 424/168

[51] Int. Cl.² ............... A61K 7/00; A61K 7/02; A61K 7/021

[58] Field of Search ............ 424/63, 69, 78, 81, 424/168; 260/29.6, 86.1; 252/309, 312, 356, 357

[56] References Cited

FOREIGN PATENTS OR APPLICATIONS 36-7038  6/1961  Japan ............................. 424/61

OTHER PUBLICATIONS

Schwartz et al., Surface Active Agents & Det., Intersci. Pub., vol. II, 1958, pp. 147, 153, 172, 614–616, 618–621, 623–625.

*Primary Examiner*—Albert T. Meyers
*Assistant Examiner*—A. P. Fagelson
*Attorney, Agent, or Firm*—Cushman, Darby & Cushman

[57] ABSTRACT

An emulsion comprises an oil phase and a water phase emulsified with an emulsifying agent consisting essentially of at least one block polymer containing both at least one lipophilic sequence and at least one hydrophilic sequence.

14 Claims, No Drawings

COSMETIC EMULSION COMPOSITIONS INCLUDING BLOCK POLYMER EMULSIFIERS

This is a continuation, of application Ser. No. 294,923 filed Oct. 4, 1972 (now abandoned) which in turn is a continuation-in-part of application Ser. No. 131,810 filed, April 6, 1971, now abandoned.

The present invention relates to new "water-in-oil" and "oil-in-water" emulsions.

Heretofore, it has been known that cosmetic products, such for example, as make-up or beauty creams could be made up in the form of a water-in-oil emulsion because the water retained in dispersion in the oily phase ensures better hydration of the epidermis in some cases, and a better protection thereof. However, it has been difficult, thus far, to sell cosmetic products of this type because water-in-oil emulsions have always entailed two kinds of difficulties.

In the first place, it is necessary that the emulsions not turn around, i.e. that they not become transformed into an oil-in-water type emulsion through aqueous dilution.

Secondly, it is necessary that the cosmetic products be sufficiently stable as emulsions to preserve their finely dispersed structures in spite of storage times that can amount to several years, and in spite of considerable temperature variations, which generally promote destruction of the emulsion by loss of the dispersed state of the aqueous phase. This is especially likely to happen in cases where the emulsions are subjected to low temperatures.

In the past it has been proposed to use as an emulsifier in such emulsions, a mixture of a hydroxypropylene alcohol-polyglycerol alcohol and magnesium isostearate, succinic esters of polyoxyalkyl fatty alcohols of hydroxypropylene-hydroxyethylene alcohols.

Moreover, it is already known that there can be used, as emulsifiers in cosmetic compositions, especially creams, polymers that are constituted by a sequence obtained by polymerization of propylene oxide, on which sequence are grafted two sequences which are obtained by polymerization of ethylene oxide. Such copolymers are known as Pluronics (sold by Wyandotte Chem. Corp.).

The applicants have now unexpectedly found that it is possible to prepare very good cosmetic emulsions using a great variety of block polymers as emulsifier. Such polymers are known and some of them have already been proposed for use as additives in motor lubricants.

It is well known that the different monomers that enter into the production of copolymers can be managed in different ways so as to lead to the formation of the polymer chain. Generally, the polymerization processes make it possible to produce a predetermined type of polymer.

In particular, with a well defined polymerization process, it is possible to prepare copolymers whose monomer sets are grouped by types, the said groups being designated as a "sequence". Such copolymers are called "block polymers" which are generally bipolymers comprising two types of sequences, each derived from identical monomers. Generally, the number of sequences is two or three.

Copolymers which contain two sequences are called "double sequenced" and the distribution of the monomer sets on the polymer chain can be represented in the following way:

AA ... AABB ... BB

Copolymers which contain three sequences are generally called "triple sequenced" and the distribution of the monomer sets on the polymer chain can be represented in the following way:

AA ... AABB ... BBAA ... AA

The present invention relates to an emulsion that can be utilized in cosmetics, or the water-in-oil type, or oil-in-water type, the said emulsion being stable and non reversible and being characterized in that it contains, as an emulsifier, a block polymer comprising simultaneously at least one lipophilic sequence and at least one hydrophilic sequence.

The lipophilic sequences are obtained from lipophilic chain monomers, while the hydrophilic sequences are obtained from monomers with hydrophilic chains.

The lipophilic sequences of the block polymer used as the emulsifier in the present invention can be represented by the following formula:

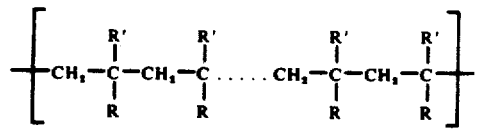

wherein

R is selected from the group consisting of:

(a)  and (b) 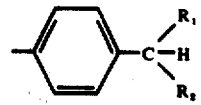

when R' represents a hydrogen and (c) 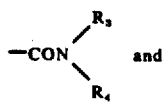 and d. — COO $R_5$ when R' represents methyl;

$R_1$ and $R_2$ each independently represent a member selected from the group consisting of hydrogen and alkyl having 1 to 4 carbon atoms, $R_3$ is a saturated hydrocarbon chain, i.e. alkyl containing 6 to 18 carbon atoms, $R_4$ is selected from the group consisting of methyl and ethyl, and $R_5$ is a saturated hydrocarbon chain, i.e. alkyl, containing 4 to 26 carbon atoms.

The hydrophilic sequences of the block polymer as the emulsifier in the present invention can be represented by the following formula:

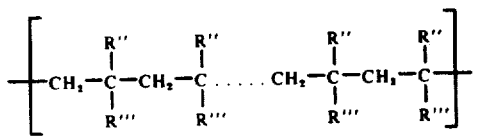

wherein
R'' is selected from the group consisting of
a. — COOH

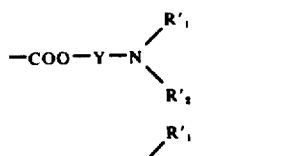

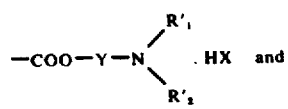

d. —C≡N
when R''' represents methyl, (e) 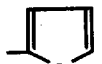

(f) 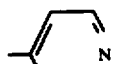

(g) 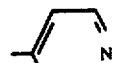

(h) 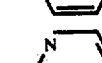

(i) 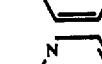

(j) 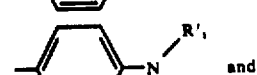
and (k) 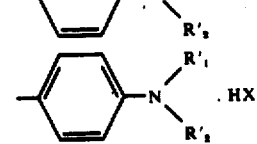

when R''' represents hydrogen,
R'₁ and R'₂ each independently are selected from the group consisting of hydrogen and lower alkyl having 1 to 4 carbon atoms,
Y is selected from the group consisting of a saturated hydrocarbon chain having 2–4 carbon atoms and a hydrocarbon chain having 2–4 carbon atoms, interrupted by a heteroatom selected from the group consisting of oxygen and sulfur,
HX represents a mineral or organic acid selected from the group consisting of hydrochloric acid, hydrobromic acid, lactic acid and acetic acid.

When R'' represents a carboxylic acid function, this function can be neutralized by a mineral or organic base such as ammonia, monoethanolamine, diethanolamine, triethanolamine, isopropyl amine, morpholine, 2-amino, 2-methyl, 1-propanol, 2-amino, 2-methyl, 1,3-propanediol, or a salinated form thereof such as the sodium, potassium or magnesium salt thereof.

Representative monomers that can be used to form lipophilic sequences, include, for instance, the following monomers: styrene, 4-methyl styrene and lauryl methacrylate.

Representative monomers that can be used to form hydrophilic sequences include, for instance, the following monomers: 2-vinyl pyridine, its hydrochloride or its lactate; 4-vinyl pyridine, its hydrochloride and its lactate; paradimethylaminostyrene, its hydrochloride and its lactate; 2-(N,N-dimethylamino) ethyl methacrylate; 2(N,N-diethylamino) ethyl methacrylate; 2-(N,N-dimethylamino) ethyl glycol methacrylate; 2-(N,N-diethylamino) ethylglycol methacrylate; and methacrylonitrile.

In a modification of the present invention, hydrophilic sequences which contain tertiary amine functions can be quaternized by means of a quaternizing agent such as, for example, dimethyl sulfate, ethyl bromide or beta bromoethanol.

The molecular weight of the block polymers used as an emulsifier in accordance with the present invention can range within wide limits. The molecular weight is generally fixed as a function of the properties sought for the emulsifier. Accordingly, the block polymers used in the present invention generally have a molecular weight ranging between about 1000 and 1,000,000 and preferably between 8,000 and 700,000.

Similarly, the proportion of the lengths of the sequences can vary within very wide limits and is generally determined by the particular application for which the copolymer is intended, namely a water-in-oil or an oil-in-water emulsion.

The block copolymers used in the present invention can also be employed in the development of oil-in-water emulsions when the polymer is water soluble while having a certain affinity for oils.

One of the most characteristic and most important of the properties of the sequenced polymers resides in that each of the sequences has the qualities of the corresponding homopolymer. By choice of the sequences, it is possible to obtain copolymers which are both hydrophilic and lipophilic but whose hydrophilic or lipophilic properties are more or less marked.

The invention also relates to a novel product of manufacture comprising a cosmetic product or an excipient for a pharmaceutical product characterized in that it has the form of a water-in-oil or oil-in-water emulsion produced by use of at least one block polymer as defined above. The amount of emulsifier, present in the emulsion of the present invention can vary within very broad limits, e.g. from 5 to 20% by weight, whereas the amount of water present can vary from about 20 to 75% by weight with reference to the total weight of the emulsion. Generally, the amount of emulsifier with reference to the oil phase which can comprise an oil or wax mixture is at least equal to 10% of said mixture.

The amount of said mixture of oil and wax, based on the total weight of the emulsion of the present invention generally ranges between 20 and 65% by weight of the total emulsion.

According to the present invention, the oil phase of the emulsion can be provided by a great variety of products. Representative materials include, for instance, hydrocarbon oils, such as paraffin oil, liquid Vaseline, perhydrosqualene, solutions of microcrystalline wax in paraffin oil and Purcellin oil; animal or vegetable oils such as horse oil, lard, sweet almond oil, callophyllum oil, olive oil, avocado oil, these oils being well absorbed by the skin; saturated esters that do not become rancid and that are satisfactorily penetrating, such as isopropyl palmitate, isopropyl myristate, ethyl palmitate, dissopropyl adipate and octa and decanoic acid triglycerides.

Silicone oils that are soluble in other oils can also be added to the oil phase as can be phenyl ethyl alcohol.

In some cases, to promote oil retention, it is desirable to use waxes such as Carnauba wax, candellila wax, beeswax, microcrystalline wax and ozokerite.

As adjuvants to the oil phase, there can also be used long chain fatty alcohols such as fatty alcohol of beeswax; cholesterol; alcohol of lanolin; or magnesium stearate.

The emulsions of the present invention make it possible to produce a wide variety of cosmetic products, such as moisturizing creams, color bases, makeup, fluid creams, brilliantines, sun-shield preparations etc.

The present invention also relates to a process for the preparation of water-in-oil and oil-in-water emulsions using the above defined emulsifiers.

This process of preparation comprises essentially mixing, in a first step, the block polymer with the oil phase accompanied by vigorous agitation at a temperature of about 150° C, and then in a second step, after cooling the copolymer and oil phase mixture to a temperature of about 80° C, introducing into said mixture the water phase, also with vigorous agitation. The water phase can, optionally, contain hydrochloric acid, lactic acid or acetic acid, and is previously brought to the same temperature. The resulting mixture is cooled to ambient temperature, with continuous stirring. At the end of the operation, the emulsion can be passed on a cylinder grinder, to refine it.

The process for the preparation of block polymers is well known and involves, for instance, the following procedure.

The polymerization reaction is generally initiated by so-called "anionic" polymerization starters of initiators which are generally metals belonging to the first group of the periodic table of elements, such as lithium, sodium, potassium etc., or organic derivatives of these metals. These can be mentioned for example compounds such as diphenylmethyl sodium, fluorenyl lithium, fluorenyl sodium, naphthalene sodium, naphthalene potassium, naphthalene lithium, tetraphenyl disodiobutane, phenylisopropyl potassium.

The choice of a particular polymerization initiator is important because it permits the determination of the desired block polymer structure. Thus, the use of naphthalene sodium directs the polymerization reaction towards the production of a "triple sequence" copolymer, while the use of phenyl isopropyl potassium directs the polymerization reaction towards the production of a "double sequence" polymer.

These polymerization reactions which lead to formation of block polymers take place in aprotic solvents, such as benzene, tetrahydrofuran, toluene, etc.

In general, the preparation of triple sequence polymers is effected in the following manner. First a solution of the initiator is prepared in the selected aprotic solvent and then one of the monomers that is to be used to prepare one of the sequences is added. After the polymerization of this polymer (a reaction that is effected generally in a few minutes), the second monomer, which is to be used to form the two other sequences, is added, the two said other sequences arranging themselves symmetrically with reference to the sequence of the first monomer. After the end of the polymerization, the triple sequence polymer is deactivated by adding a few drops of methanol to the reaction mixture. In general, the reaction which leads to the formation of these block polymers is effected at a temperature of about −70° C.

These polymerization reactions for production of block polymers obviously cannot be effected with monomers having replaceable hydrogen, for example, acids, amides, etc. Consequently, if it is desired to produce block polymers which, in one of their sequences, have acid, amide, and the like functions, it is necessary to start with monomers that can finally produce, by chemical reaction, these kinds of functions. It is possible to start, for example, with monomers which have a nitrile function or an ester function. By hydrolysis, it is possible to obtain corresponding acids, and finally, by amidification, to obtain the corresponding amides. Such a procedure can be used when it is desired to produce lipophilic sequences constituted by methacrylamide radicals or to produce hydrophilic sequences constituted by methacrylic acid radicals.

The following examples illustrate the present invention. The emulsion compositions which are described in these examples are, in each case, obtained by the methods described above.

EXAMPLE 1

Preparation of a double sequence 2-vinyl pyridine lauryl methacrylate polymer

In a two liter vessel furnished with mechanical agitator, two dropping funnels a graduated tube, a nitrogen supply tube, an immersion tube for sampling the reaction mixture in the course of reaction, and a thermometer, there is introduced one liter of anhydrous distilled tetrahydrofuran. The vessel is then cooled to −70° C with a mixture of methanol and dry ice.

The apparatus assembly is in a nitrogen atmosphere which is carefully purified by heating to 400° C in the presence of copper foil, the nitrogen stream likewise being purified by passage over anhydrous potassium and over perchlorate of anhydrous magnesium.

Through the graduated tube, there is added drop by drop, with agitation, a solution of diphenyl methyl sodium in distilled anhydrous tetrahydrofuran. At the start of the addition, the diphenyl methyl sodium solution loses color as soon as it comes into contact with the tetrahydrofuran in the vessel. Introduction of the diphenyl methyl sodium solution is then continued until a yellow red coloration persists in the reaction vessel. There is then introduced via the same graduated tube an additonal 2.82 ml of a solution that contains 247 mg diphenyl methyl sodium in tetrahydrofuran, all under nitrogen atmosphere.

Through one of the dropping funnels there are rapidly introduced into the reaction vessel, under nitrogen and with agitation, 30.3 g of carefully purified 2-vinyl pyridine.

The temperature inside the vessel rises to −62° C in the course of several minutes, while the coloration of the reaction mixture becomes darker.

By means of the immersion tube, a small amount of the "live" polymer solution is suctioned off. This live 2-vinyl pyridine in tetrahydrofuran serves for calculation of mass by weight.

As soon as the internal temperature of the vessel goes down, there are rapidly introduced via the other dropping funnel, under nitrogen, 22.4 g of carefully purified lauryl methacrylate. The temperature rises to about −62° C and after the exothermal character of the polymerization tapers off, the double sequence polymer is deactivated, the two sequences comprising lauryl polymethacrylate and polyvinyl-2-pyridine. In general, this last stage is effected by means of a few drops of methanol. The solution then becomes practically colorless. The tetrahydrofuran is distilled off and the residual polymer is dissolved in chloroform and then precipitated by petroleum ether. After two dissolvings in chloroform and two precipitations by petroleum ether, the polymer is vacuum dried.

There is thus obtained 30 g dry polymer (60% yield). The mass by weight of this copolymer, determined by light diffusion in methanol solution, is:

$M_p = 110,000$, $d_n d_c$ (MeOH) = 0.184

The sampling of the homopolymer of polyvinyl-2-pyridine, deactivated with methanol and purified according to the method used for purification of the double sequence polymer, allows determination of its mass by weight by the same method:

$M_p = 60,000$, $d_n/d_c$ (MeOH) = 0.236.

The polymers of table I and II below were prepared according to the operative procedure as described above.

TABLE I

| | | | \multicolumn{2}{c|}{DOUBLE SEQUENCED BLOCK COPOLYMERS} | | | | | | |
|---|---|---|---|---|---|---|---|---|---|---|
| Copoly-mer No. | Monomer 1 | Monomer 2 | Quantity of Monomer 1 (g) | Quantity of Monomer 2 (g) | Solution Catalyst in Tetra-hydro-furan (ml) | Quantity of Catalyst (mg) | Rdt % | Average Molecular Weight | $\frac{dn}{dc}$ (THF) | Analysis % | L/H Weight Ratio in the block polymer |
| 2 | 2-Vinyl pyridine (H) | Lauryl meth-acrylate (L) | 30 | 15 | 20 | 1,632(a) | 45 | 967,000 | 0.113 | C 73 H 9.6 N 4.5 | 66/34 |
| 3 | 2-(N,N-dimethyl amino) ethyl-methacry-late (H) | " (L) | 7 | 12.5 | 30 | 4,400(a) | 41 | 8,000 | 0.079 | C 74.4 H 11.6 N 0.9 | 90/10 |
| 4 | " (H) | " (L) | 7 | 12.5 | 6 | 430(a) | 15.8 | 109,000 | 0.079 | C 74.5 H 11.4 N 0.9 | 90/10 |
| 5 | " (H) | " (L) | 7 | 27.5 | 6 | 430(a) | 32 | 254,000 | 0.079 | C 74.5 H 11.4 N 0.8 | 91/9 |
| 6 | Styrene (L) | 2-Vinyl pyridine (H) | 7 | 5 | 25 | 1,260(b) | 67 | 15,400 | 0.181 | C 87.9 H 7.6 N 4.1 | 31/69 |
| 7 | " (L) | " (H) | 7 | 10 | 25 | 1,260(b) | 80 | 270,000 | 0.182 | C 85.1 H 7.5 N 6 | 50/50 |

N.B:
The letter "L" represents lipophile
The letter "H" represents hydrophile
(a)diphenyl methyl sodium
(b)phenyl isopropyl potassium
The preparation of these double sequenced block copolymers is carried out by homopolymerizing monomer 1 and then copolymerizing the resulting homopolymer with monomer 2.

TABLE II

| Co-poly-mer No. | Mono-mer 1 | Mono-mer 2 | Type of copoly-mer | Quantity of Monomer 1 (g) | Quantity of Monomer 2 (g) | Solu-tion of cata-lyst in tetra-hydr-ofu-ran (ml) | Qua-ntity of cata-lyst (mg) nap-htha-lene sod-ium | Rdt % | Average Mole-cular Weight | $\frac{dn}{dc}$ (THF) | Analysis (%) C H N | L/H ratio Weight in the block copolymer |
|---|---|---|---|---|---|---|---|---|---|---|---|---|
| 8 | Styrene (L) | 2-vinyl pyridine (H) | H—HL—LH—H | 20 | 5 | 12 | 543 | 80 | 52,000 | 0.182 | 91.3 9.0 <1 | >93/7 |
| 9 | " (L) | " (H) | H—HL—LH—H | 20 | 13 | 12 | 543 | 76 | 57,000 | 0.174 | 84.1 7.3 7.7 | 42/58 |
| 10 | "(L) | "(H) | H—HL—LH—H | 20 | 0 | 12 | 543 | 74 | 50,000 | 0.178 | 89.5 7.8 2.4 | 82/18 |
| 11 | 4-methyl styrene (L) | 4-vinyl pyridine (H) | H—HL—LH—H | 6 | 1.5 | 3 | 408 | 40 | 55,000 | 0.183 | 91 8 <1 | >93/7 |
| 12 | "(L) | "(H) | H—HL—LH—H | 6 | 4 | 3 | 408 | 35 | 71,000 | 0.167 | 89.7 8 1.3 | 89.9/9.1 |
| 13 | styrene (L) | 2-(N,N-dimethyl amino) ethyl methacry- | H—HL—LH—H | 20 | 5 | 12 | 543 | 60 | 78,000 | 0.153 | 82.5 8.5 2.6 | 71/29 |

TABLE II-continued

Triple Sequenced Block Copolymers

| Copolymer No. | Monomer 1 | Monomer 2 | Type of copolymer | Quantity of Monomer 1 (g) | Quantity of Monomer 2 | Solution of catalyst in tetrahydrofuran (ml) | Quantity of catalyst (mg) naphthalene sodium | Rdt % | Average Molecular Weight | dn/dc (THF) | Analysis (%) C | H | N | L/H ratio Weight in the block copolymer |
|---|---|---|---|---|---|---|---|---|---|---|---|---|---|---|
| 14 | "(L) | late (H) "(H) | H—HL—LH—H | 20 | 13 | 12 | 543 | 55 | 196,000 | 0.142 | 77.3 | 8.5 | 2.6 | 58.5/41.5 |
| 15 | "(L) | "(H) | H—HL—LH—H | 20 | 30 | 12 | 543 | 50 | 202,000 | 0.131 | 74.5 | 7.0 | 4.5 | 49.5/50.5 |
| 16 | 2-vinyl pyridine (H) | Lauryl Methacrylate (L) | L—LH—HL—L | 11 | 5 | 6 | 816 | 50 | 40,000 | 0.150 | 76.4 | 9.5 | 5.3 | 61/39 |
| 17 | "(H) | "(L) | L—LH—HL—L | 11 | 11 | 6 | 816 | 41 | 46,000 | 0.116 | 76.4 | 9.7 | 5.4 | 60/40 |
| 18 | Lauryl methacrylate (L) | 2-(N,N-dimethyl amino)ethyl methacrylate (H) | H—HL—LH—H | 5 | 2 | 6 | 816 | 20 | 730,000 | 0.082 | 58.9 | 9.2 | 6.8 | 27/75 |
| 19 | "(L) | "(H) | H—HL—LH—H | 5 | 5 | 6 | 816 | 40 | 880,000 | 0.080 | 61.4 | 9.8 | 7.4 | 17/83 |
| 20 | Styrene (L) | 4-vinyl pyridine (H) | H—HL—LH—H | 5 | 3 | 3 | 407 | 44 | 66,000 | 0.189 | 92.2 | 7.5 | <1 | >92.5/7.5 |
| 21 | "(L) | "(H) | H—HL—LH—H | 5 | 10 | 3 | 407 | 27 | 65,000 | 0.195 | 92.7 | 7 | <1 | >92.5/7.5 |
| 22 | "(L) | 2-(N,N-dimethyl amino)ethyl methacrylate | H—HL—LH—H | 20 | 2 | 12 | 543 | 60 | 78,000 | 0.153 | 82.5 | 8.5 | 2.6 | 71/29 |

N.B.
The preparation of these triple sequenced block copolymers is carried out by homopolymerizing monomer 1 and then copolymerizing the resulting homopolymer with monomer 2

L represents lipophile and H represents hydrophile.

EXAMPLE 23

Preparation of a double sequence polymer of butyl methacrylate and dimethylaminoethyl In a two liter round reaction vessel provided with a mechanical agitator, two dropping funnels, a graduated tube, a nitrogen supply tube, an immersion tube for sampling the reaction mixture in the course of the reaction, and a thermometer, there is introduced one liter of anhydrous distilled tetrahydrofuran. The reaction vessel is then cooled to −70° C with a mixture of dry ice and methanol.

The apparatus assembly is maintained in a nitrogen atmosphere which is carefully purified by heating to 400° C in the presence of copper foil, the nitrogen stream also being purified by passage over anhydrous potassium and over perchlorate of anhydrous magnesium.

Through the graduated tube, there is added drop by drop, with agitation, a solution of cumyl potassium in distilled anhydrous tetrahydrofuran. At the start of the addition, the cumyl potassium loses color as soon as it comes into contact with the tetrahydrofuran in the reaction vessel. Introduction of the solution of cumyl potassium is then continued until a red color persists in the reaction vessel. There is then introduced via the same graduated tube and additional 30 ml of a solution containing 334 mg of cumyl potassium in tetrahydrofuran, all under the nitrogen atmosphere.

Through one of the dropping funnels, there are rapidly introduced into the reaction vessel, under nitrogen atmosphere and with agitation, 30 g of carefully purified butyl methacrylate. The temperature within the reaction vessel rises to −60° C for a few minutes while the color of the reaction mixture becomes clear.

As soon as the internal temperature of the reaction mixture goes down there are rapidly introduced via the other dropping funnel under nitrogen, 30 g of carefully purified dimethylaminoethyl methacrylate. The temperature rises to about −60° C and after the exothermal character of the polymerization reaction tapers off, the double sequence polymer is deactivated, the two sequences comprising butyl polymethacrylate and dimethylaminoethyl polymethacrylate. Generally this last stage is effected by means of a few drops of methanol. The solution then becomes practically colorless and the polymer percipitated by water. The polymer is rapidly filtered with pentane and then it is dried under reduced pressure.

There is thus obtained 30 g of the dry polymer (60% yield). The molecular weight of the polymer is determined by the light diffusion is:

$$\overline{M}_p = 40,000$$

Using the same method of operation as in preceding Example 23, there are prepared the following triple sequenced polymers:

| Ex. | Monomer 1 | Monomer 2 | Type of Copolymer | Quantity (g) Monomer 1 | Monomer 2 | Quantity of (mg) catalyst Naphthalene sodium (mg) | Yield | Molecular weight | L/H Weight ratio in the copolymer |
|---|---|---|---|---|---|---|---|---|---|
| 24 | Butyl methacrylate | 2-vinyl pyridine | H—HL—LH—H | 25 | 25 | 302 | 80 | 65,000 | 55/45 |

-continued

| Ex. | Monomer 1 | Monomer 2 | Type of Copolymer | Quantity (g) Monomer 1 | Quantity (g) Monomer 2 | Quantity of (mg) catalyst Naphthalene sodium (mg) | Yield | Molecular weight | L/H Weight ratio in the copolymer |
|---|---|---|---|---|---|---|---|---|---|
| 25 | (L) Butyl methacrylate (L) | (H) 4-vinyl pyridine (H) | H—HL—LH—H | 25 | 25 | 360 | 40 | 55,000 | 53/47 |

EXAMPLES OF COMPOSITION

Example A

There is prepared according to the invention a liquid cream having the following composition:

| | |
|---|---|
| Copolymer No. 3 | 7 g |
| Paraffin oil | 40 g |
| Microcrystalline wax | 3 g |
| Water | 50 g |

Example B

There is prepared according to the invention a color base having the following composition:

| | |
|---|---|
| Copolymer as in Example 1 | 7.4 g |
| Paraffin oil | 20 g |
| Perhydrosqualene | 24 g |
| Titanium oxide | 1.5 g |
| Ocher | 1.5 g |
| Perfume | 0.2 g |
| Water + lactic acid (3.4 g) | 45.4 g |

Example C

A night cream, prepared according to the invention, has the following composition:

| | |
|---|---|
| Copolymer as in Example 1 | 7 g |
| Paraffin oil | 22.1 g |
| Isopropyl palmitate | 10 g |
| Purcellin oil | 12 g |
| Bleached ozokerite | 2.5 g |
| Water + hydrochloric acid (1.4 g) | 46.4 g |

Example D

There is prepared according to the invention a milk of the following composition:

| | |
|---|---|
| Copolymer No. 4 | 12 g |
| Paraffin oil | 18 g |
| Liquid Vaseline | 8 g |
| Octa and decanoic triglyceride | 10 g |
| Ozokerite | 2 g |
| Water + acetic acid | 50 g |

Example E

There is prepared according to the invention, a face makeup having the following composition:

| | |
|---|---|
| Copolymer No. 10 | 15 g |
| Liquid Vaseline | 6 g |
| 2-octyl 1-dodecanol | 2 g |
| Isopropyl palmitate | 5 g |
| Diisopropyl adipate | 37.4 g |
| Candellila wax | 2.5 g |
| Carnauba wax | 2 g |
| D and C red No. 8 (dye) | 0.5 g |

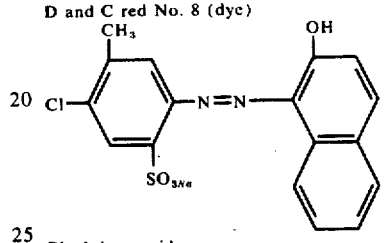

| | |
|---|---|
| Black iron oxide | 0.1 g |
| Titanium oxide | 1.5 g |
| Water | 28 g |

Example F

A moisturizing sun milk, prepared according to the invention, has the following composition:

| | |
|---|---|
| Copolymer No. 11 | 10 g |
| Octa and decanoic triglyceride | 6 g |
| Isopropyl myristate | 11 g |
| Diisopropyl adipate | 30 g |
| Ozokerite | 2 g |
| "Parsol-Ultra" a mixture of esters of substituted aminobenzoic acids and esters of substituted cinnamic acids, sold by GIVAUDAN company (sun filter) | 2 g |
| Water + lactic acid (0.6 g) | 39 g |

Example G

A colored "open air" cream, prepared according to the invention, has the following composition:

| | |
|---|---|
| Copolymer No. 13 | 10 g |
| Isopropyl palmitate | 7 g |
| Diisopropyl adipate | 28 g |
| Paraffin oil | 6 g |
| Beeswax | 2 g |
| Red iron oxide | .1 g |
| Yellow iron oxide | 1 g |
| Titanium oxide | 1 g |
| Water + hydrochloric acid (0.7 g) | 44 g |

Example H

A nail base cream, prepared according to the invention, has the following composition:

| | |
|---|---|
| Copolymer No. 16 | 7 g |
| Isopropyl palmitate | 20 g |
| Perhydrosqualene | 30 g |
| Liquid Vaseline | 7 g |
| Carnauba wax | 3 g |
| 2-octyl 1-dodecanol | 3 g |

| Water | 30 g |

Example I

An oil-in-water makeup remover cream, prepared according to the invention, has the following composition:

| Copolymer No. 18 | 6 g |
|---|---|
| Octa and decanoic triglyceride | 18 g |
| Isopropyl palmitate | 5 g |
| Paraffin oil | 2 g |
| Water | 69 g |

The emulsions of the invention lend themselves especially well to the preparation of a color base, makeup and hand creams.

It will be appreciated that several emulsifiers of the invention can be used simultaneously and that, if desired, they can be employed with other emulsifiers which have previously been known. It is likewise obvious that there can be introduced into the emulsions of the invention, ingredients that are generally used in cosmetic formulations, especially those that tend to increase the stability and properties of preservation. Finally, it is understood that the emulsions of the invention can also be used in fields other than those of cosmetics and excipients for pharmaceutical products.

Example J

A cream, prepared according to the invention, has the following composition:

| Copolymer No. 9 | 15 g |
|---|---|
| Ethyl phenyl alcohol | 40 g |
| Diisopropyl adipate | 7 g |
| Water + acetic acid (4 g) | 38 g |

Example K

A cream, prepared according to the invention, has the following composition:

| Copolymer No. 6 | 13 g |
|---|---|
| Diisopropyl palmitate | 5 g |
| 2-octyl 1-dodecanol | 5 g |
| Liquid Vaseline | 1 g |
| Diisopropyl adipate | 26 g |
| Ozokerite | 2 g |
| Water | 42 g |

Example L

A cream, prepared according to the invention, has the following composition:

| Copolymer No. 3 | 10 g |
|---|---|
| Perhydrosqualene | 25 g |
| Liquid Vaseline | 14.5 g |
| Ozokerite | 3 g |
| Water | 47.5 g |

Example M

A fluid cream is prepared in accordance with the present invention by admixing the following components:

| Copolymer prepared according to Example 23 | 15 g |
|---|---|
| Octa and decanoic triglyceride extracts of coconut oil | 35 g |
| Paraffin oil | 6 g |
| Isopropyl palmitate | 8 g |
| Microcrystalline wax | 3 g |
| Water | 33 g |

Example N

A cream is prepared in accordance with the present invention by mixing the following components:

| Oleyl alcohol oxyethylenated with two moles of ethylene oxide | 8 g |
|---|---|
| Copolymer prepared according to Example 24 | 2 g |
| Paraffin oil | 19 g |
| Isopropyl myristate | 10 g |
| Perhydrosqualene | 20 g |
| Microcrystalline wax | 3 g |
| Water | 38 g |

Example O

A cream is prepared in accordance with the following example by mixing the following components:

| Oleyl alcohol oxyethylenated with two moles ethyl oxide | 8 g |
|---|---|
| Copolymer prepared according to Example 25 | 2 g |
| Paraffin oil | 19 g |
| Isopropyl myristate | 10 g |
| Perhydrosqualene | 20 g |
| Microcrystalline wax | 3 g |
| Water | 38 g |

What is claimed is:

1. A cosmetic composition in the form of a cream, a color base or a milk comprising an emulsion of an oil phase and a water phase emulsified with an emulsifying agent, wherein said oil is selected from the group consisting of animal oil, vegetable oil, hydrocarbon oil and mixtures thereof and wherein said emulsifying agent consists essentially of at least one block polymer containing:

A. at least one lipophilic sequence of the formula

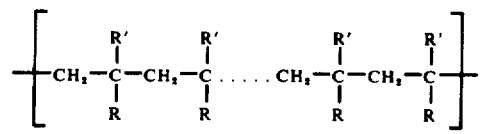

wherein R' is selected from the group consisting of hydrogen and methyl, and wherein when R' is hydrogen, R is selected from the group consisting of:

(a) 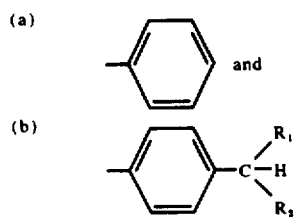 and (b) 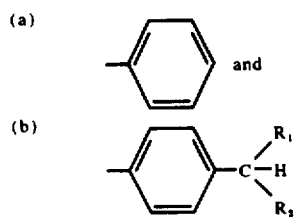

and wherein when R' is methyl, R is selected from the group consisting of (c) 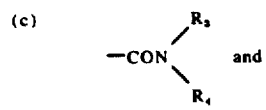 and d. — COO R₅ and wherein
R₁ and R₂, each independently, represent a member selected from the group consisting of hydrogen and alkyl having 1 to 4 carbon atoms,
R₃ is alkyl containing 6 to 18 carbon atoms,
R₄ is selected from the group consisting of methyl and ethyl, and R₅ is lauryl, and (b) at least one hydrophilic sequence of the formula

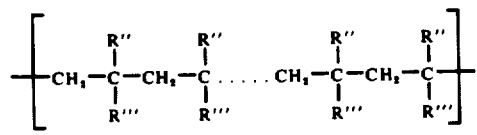

wherein
R''' is selected from the group consisting of hydrogen and methyl, and wherein when R''' is methyl,
R'' is selected from the group consisting of
a. — COOH (b) 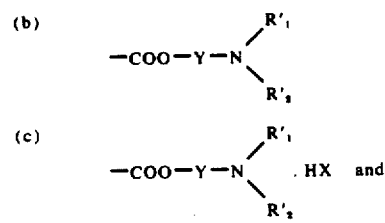

(c) 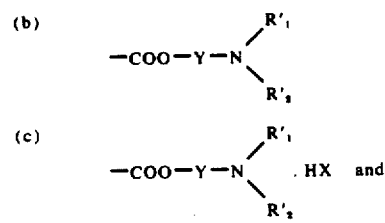 . HX and d. — C ≡ N when R''' is hydrogen, R'' is selected from the group consisting of (e) 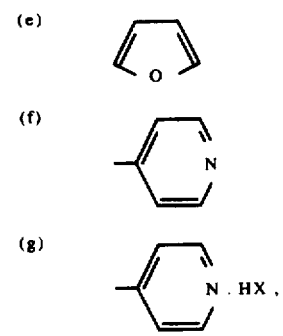

(f) 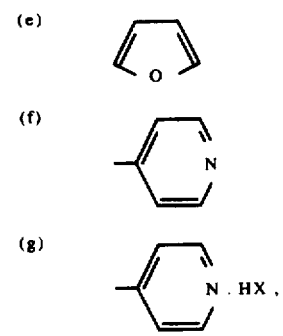

(g) 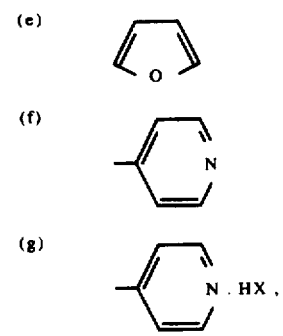 . HX , (h) 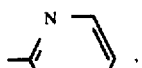 .

(i)  . HX , (j) 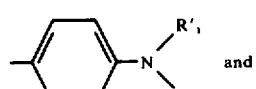 and (k) 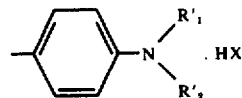 . HX

R'₁ and R'₂, each independently selected from the group consisting of hydrogen and lower alkyl having 1 to 4 carbon atoms,
Y is selected from the group consisting of a saturated hydrocarbon chain having 2–4 carbon atoms and a hydrocarbon chain having 2–4 carbon atoms interrupted by a heteroatom selected from the group consisting of oxygen and sulfur, and
HX represents a mineral or organic acid selected from the group consisting of hydrochloric acid, hydrobromic acid, lactic acid and acetic acid.

2. The composition of claim 1 where in the hydrophilic sequence R'' is a free carboxylic acid function neutralized with a mineral base or an organic base.

3. The composition of claim 1, where in the hydrophilic sequence R' is a free carboxylic acid function in the form of a sodium, potassium or magnesium salt thereof.

4. The composition of claim 1, wherein the lipophilic sequence is formed from the polymerization of a lipophilic monomer selected from the group consisting of styrene, 4-methyl styrene, and lauryl methacrylate.

5. The composition of claim 1 wherein the hydrophilic sequences are formed from the polymerization of hydrophilic monomers selected from the group consisting of 2-vinyl pyridine, its hydrochloride and its lactate; 4-vinyl pyridine, its hydrochloride and its lactate; paradimethylaminostyrene, its hydrochloride and its lactate; 2-(N,N-dimethylamino)-ethanol methacrylate; 2-(N,N-diethylamino)-ethanol methacrylate; 2-(N,N-dimethylamino)-ethylglycol methacrylate, 2-(N,N-diethylamino) ethylglycol methacrylate; and methacrylonitrile.

6. The composition of claim 1 wherein the hydrophilic sequences contain a tertiary amine function quaternized by a quaternizing agent.

7. The composition of claim 1 wherein said quaternizing agent is selected from the group consisting of dimethyl sulfate, ethyl bromide and beta bromoethanol.

8. The composition of claim 1 wherein said block polymer has a molecular weight between 1,000 and 1,000,000.

9. The composition of claim 1 wherein said emulsifying agent is present in amounts of about 5–20% by weight of said emulsion.

10. The composition of claim 1 wherein said emulsifying agent is present in amounts of about 10% by weight of said oil phase.

11. The composition of claim 1 wherein said oil phase is present in amounts of about 20–65% by weight of said emulsion.

12. The composition of claim 1 wherein said water phase is present in amounts of about 20–75% of said emulsion.

13. The composition of claim 1 wherein said oil phase comprises at least one ingredient selected from the group consisting of paraffin oil, perhydrosqualene, solutions of microcrystalline wax in paraffin oil horse oil, lard, oil of sweet almond, callophylum oil, olive oil, avocado oil, isopropyl palmitate, isopropyl myristate, ethyl palmitate, diisopropyl adipate and triglycerides of octa and decanoic acids.

14. The composition of claim 1, wherein said oil phase also contains a wax selected from the group consisting of carnauba wax, candellila wax, beeswax, microcrystalline wax and ozokerite.

* * * * *